United States Patent
Augustyn et al.

(10) Patent No.: US 11,253,388 B2
(45) Date of Patent: Feb. 22, 2022

(54) OSTOMY BARRIER

(71) Applicant: Hollister Incorporated, Libertyville, IL (US)

(72) Inventors: Christina Augustyn, Chicago, IL (US); Ronald S. Botten, Gurnee, IL (US); Meagan R. Pheil, Chicago, IL (US); Peter L. Visconti, Gurnee, IL (US); Russell J Todd, Evanston, IL (US); Lynn Sacramento, Libertyville, IL (US); Heather M. Budorick, Glenview, IL (US); Mark W. Jockel, Chicago, IL (US)

(73) Assignee: Hollister Incorporated, Libertyville, IL (US)

( * ) Notice: Subject to any disclaimer, the term of this patent is extended or adjusted under 35 U.S.C. 154(b) by 717 days.

(21) Appl. No.: 16/086,879

(22) PCT Filed: Apr. 19, 2017

(86) PCT No.: PCT/US2017/028292
§ 371 (c)(1),
(2) Date: Sep. 20, 2018

(87) PCT Pub. No.: WO2017/184690
PCT Pub. Date: Oct. 26, 2017

(65) Prior Publication Data
US 2019/0099284 A1 Apr. 4, 2019

Related U.S. Application Data

(60) Provisional application No. 62/325,184, filed on Apr. 20, 2016.

(51) Int. Cl.
*A61F 5/448* (2006.01)
*A61F 5/443* (2006.01)
*A61F 5/449* (2006.01)

(52) U.S. Cl.
CPC .............. *A61F 5/448* (2013.01); *A61F 5/443* (2013.01); *A61F 5/449* (2013.01); *A61F 2005/4483* (2013.01)

(58) Field of Classification Search
CPC .. A61F 5/448; A61F 2005/4483; A61F 5/443; A61F 5/449
See application file for complete search history.

(56) References Cited

U.S. PATENT DOCUMENTS

| 3,123,074 | A |   | 3/1964 | Turner |
| 6,106,507 | A | * | 8/2000 | Botten ................... A61F 5/448 604/336 |

(Continued)

FOREIGN PATENT DOCUMENTS

| EP | 2496193 A1 | 9/2012 |
| JP | H06285103 A | 10/1994 |

(Continued)

OTHER PUBLICATIONS

International Preliminary Report on Patentability issued by IB of WIPO in connection with PCT/US2017/028292 dated Oct. 23, 2018.

*Primary Examiner* — Susan S Su
(74) *Attorney, Agent, or Firm* — Levenfeld Pearlstein, LLC

(57) ABSTRACT

An ostomy barrier includes an adhesive layer having a body-facing side, a distal side opposite to the body-facing side, and an opening, a seal substantially aligned with the opening, the seal having an aperture configured to receive a stoma therein, and a flexible connector extending between the seal and the adhesive layer to connect the seal to the adhesive layer. The flexible connector formed from a flexible material to allow relative movement between the seal and the adhesive layer.

19 Claims, 4 Drawing Sheets

(56) References Cited

U.S. PATENT DOCUMENTS

| | | | |
|---|---|---|---|
| 6,520,943 B1 | 2/2003 | Wagner | |
| 6,589,222 B1 * | 7/2003 | Olsen | A61F 5/443 |
| | | | 604/336 |
| 2011/0213321 A1 * | 9/2011 | Fattman | A61F 5/448 |
| | | | 604/344 |
| 2012/0323192 A1 * | 12/2012 | Willoughby | A61F 5/44 |
| | | | 604/337 |

FOREIGN PATENT DOCUMENTS

| | | |
|---|---|---|
| JP | 2002516146 A | 6/2002 |
| JP | 2002537067 A | 11/2002 |
| WO | 2011050816 A1 | 5/2011 |
| WO | 2012079592 A1 | 6/2012 |
| WO | 2015116651 A1 | 8/2015 |

\* cited by examiner

OSTOMY BARRIER

This is a National Stage Application of International Patent Application No. PCT/US2017/028292, filed Apr. 19, 2017, which claims the benefit of and priority to U.S. Provisional Application No. 62/325,184, filed Apr. 20, 2016, the entirety of which are incorporated fully herein by reference.

BACKGROUND

The following description generally relates to ostomy appliances, and in particular, an ostomy barrier.

Ostomy pouches for collecting bodily waste are used by a person who has had surgery such as a colostomy, ileostomy, or urostomy. Typically, an ostomy pouch is attached to a user via an ostomy barrier including an adhesive layer. The ostomy pouch may be provided as a single-piece pouch system including an ostomy barrier sealed to a pouch. The ostomy pouch may also be provide as a two-piece system including an ostomy barrier comprising a body-side coupling ring and a pouch comprising a pouch-side coupling ring. The body-side coupling ring and the pouch side coupling ring may be configured to engage with each other to secure the pouch to the ostomy barrier attached to a user. The ostomy barrier may be configured to adhere to user's body to support the pouch and to seal around the peristomal region to, for example, prevent leakage of effluent from the stoma. An additional sealing element may be provided for contacting and sealing around the stoma.

The topography of stomas and peristomal surfaces surrounding stomas vary among people with an ostomy, and sealing the ostomy appliances against such different peristomal surfaces and stomas remains as an area for further improvements. For example, a stoma's protrusion can vary, or may even be flush or recessed. A user with an ostomy having a stoma that is flush or recessed might find that applying external support or pressure from a barrier in the peristomal region may aid in directing the discharge of effluent from the stoma directly into the ostomy pouch. Accordingly, an effectiveness of an adhesive seal between the faceplate and the peristomal skin surface (i.e., a seal formed by the adhesive layer) may be prolonged. Thus, convex inserts and convex rings, such as ADAPT® convex barrier rings available through the assignee of the present application, have been developed to apply pressure or support around such peristomal regions.

However, the conventional convex barriers are firm and do not flex or move with the body. Thus, in normal movement of the user wearing the ostomy system, or when a force is imparted on a component of the ostomy system, the force may be transmitted to the convex barrier, and in turn the stoma. These forces may cause discomfort to the user, weaken the adhesion of the faceplate to the user's skin, and/or disrupt the seal around the stoma.

Other arrangements include a corrugation in an ostomy barrier, which may allow for movement of an ostomy barrier relative to the peristomal region. However, in this arrangement, the ostomy barrier is still adhered to the user's body in its entirety. Thus, the same drawbacks discussed above exist.

Accordingly, it is desirable to provide an ostomy barrier having a sealing function that is decoupled from an ostomy pouch support function.

SUMMARY

According to one aspect, there is provided an ostomy barrier including an adhesive layer provided on a backing layer with an opening defined therein, a seal substantially aligned with the opening, the seal having an aperture configured to receive a stoma therein, and a flexible connector extending between the seal and the adhesive layer to connect the seal to the adhesive layer. The flexible connector may be formed from a flexible material to allow relative movement between the seal and the adhesive layer.

The seal may be convex in shape or generally flat. The flexible connector may be formed from an elastic material. In an embodiment, the seal may be formed from a soft and flexible moldable material. In another embodiment, the seal may be formed from a hydrocolloid adhesive. In yet another embodiment, the seal may include an adhesive layer and a reinforcement layer. In such an embodiment, the reinforcement layer may be formed from a thermoplastic material and have a convex profile. The adhesive layer may be formed from a hydrocolloid adhesive and arranged on a body-facing side of the reinforcement layer. In some embodiments, the adhesive layer and the backing layer may be formed from a nonwoven tape, in which the adhesive layer may be formed from a different material than the seal material.

According to another aspect, an ostomy barrier may include an adhesive layer provided on a backing layer with an opening defined therein, first and second seals, and first and second flexible connectors. The second seal may be substantially aligned with the first opening and include a second opening defined therein. The first seal may be substantially aligned with the second opening and include an aperture configured to receive a stoma therein. The first flexible connector may extend between the first seal and the second seal to connect the first seal to the second seal. The second flexible connector may extend between the second seal and the adhesive layer to connect the second seal to the adhesive layer. Each of the first and second flexible connectors is formed from a flexible material to allow relative movement between the first seal, the second seal, and the adhesive layer.

In an embodiment, each of the first and second seals may be generally flat. In another embodiment, the first seal may have a convex shape, while the second seal may be generally flat. Each of the first and second flexible connectors may be formed from an elastic material. Further, each of the first and second seals may be formed from a soft and flexible moldable material. In an embodiment, each of the first and second seals is formed from a hydrocolloid adhesive. In yet another embodiment, the first seal may include an adhesive layer and a reinforcement layer, in which the reinforcement layer may be formed from a thermoplastic material having a convex profile, and the adhesive layer may be arranged on a body-facing side of the reinforcement layer. The adhesive layer of the first seal and the second seal may be formed from a hydrocolloid adhesive.

In any of the foregoing embodiments, the ostomy barrier may have a body-facing side and a distal side opposite the body-facing side, in which the adhesive layer may be arranged on the body-facing side and the backing layer is arrange on the distal side. Each of the seal may be configured to be movable relative to the adhesive layer from the body-facing side to the distal side.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
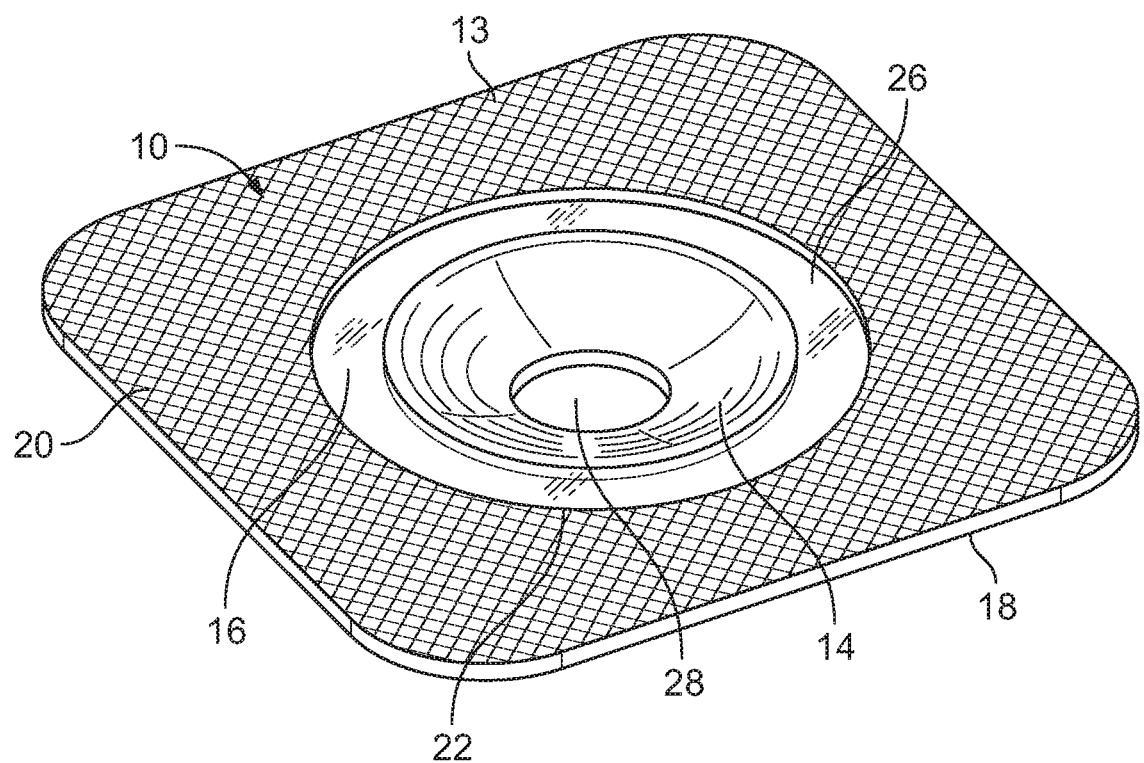
FIG. 1 is a perspective view of an ostomy barrier according to an embodiment described herein.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 2:
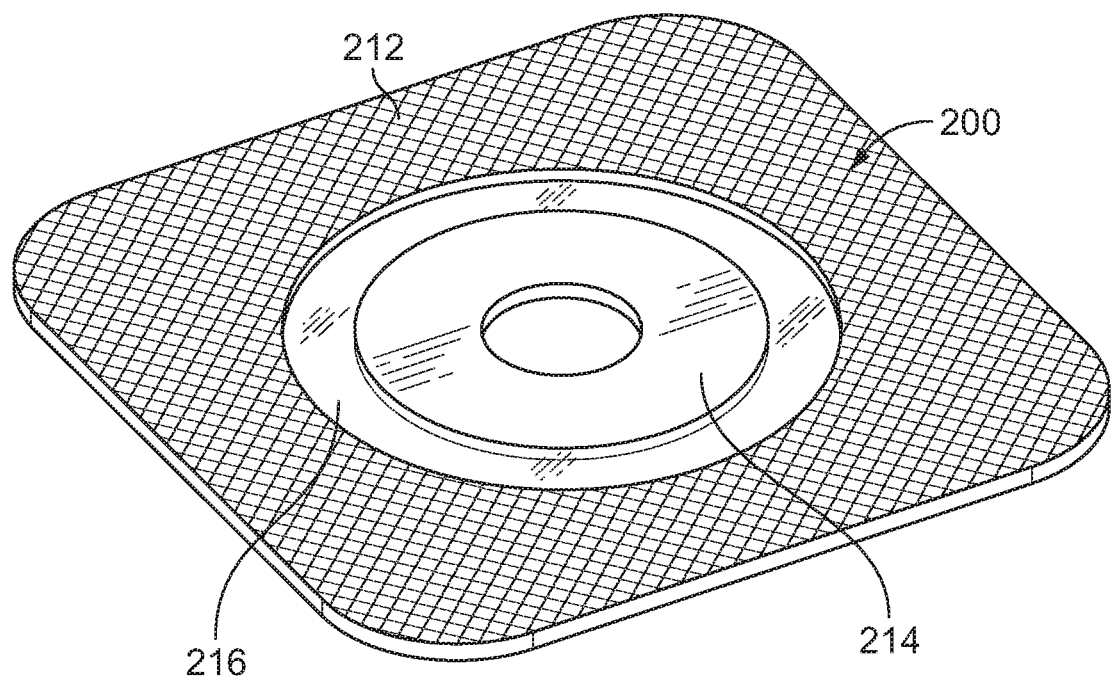
FIG. 2 is a cross-sectional view of the ostomy barrier of FIG. 1.
Figure 4:
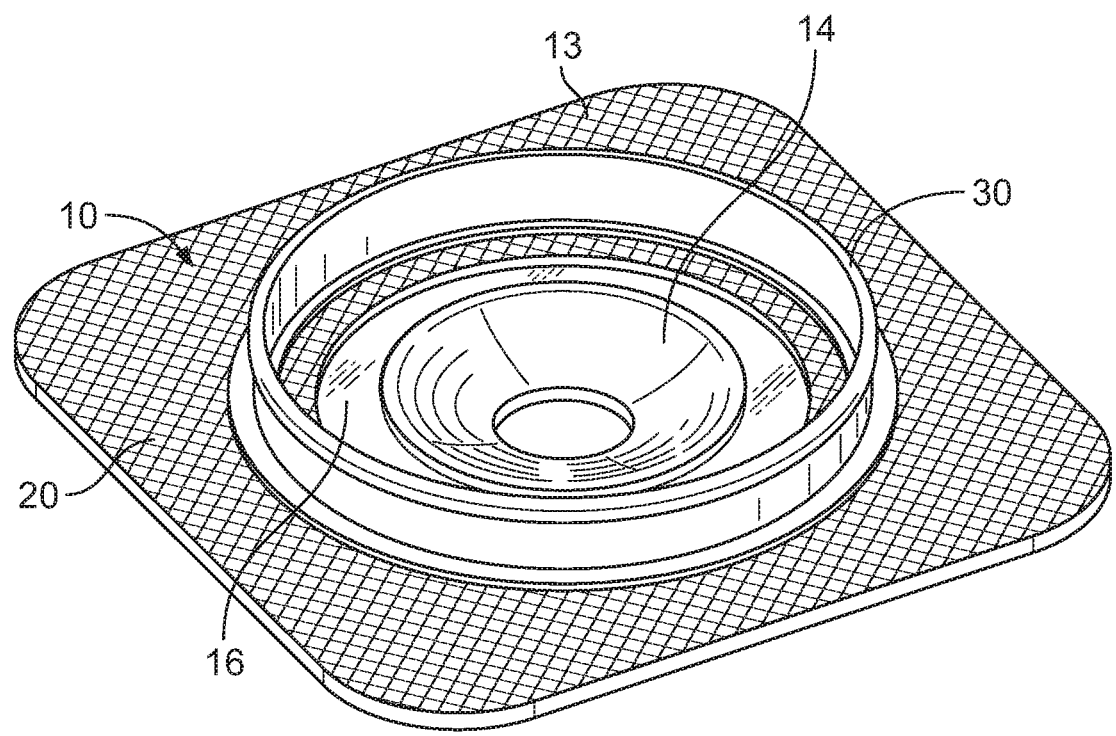
FIG. 4 is a perspective view of the ostomy barrier of FIGS. 1-2 configured for a two-piece ostomy pouch system including a body-side coupling ring according to an embodiment.
Figure 5:
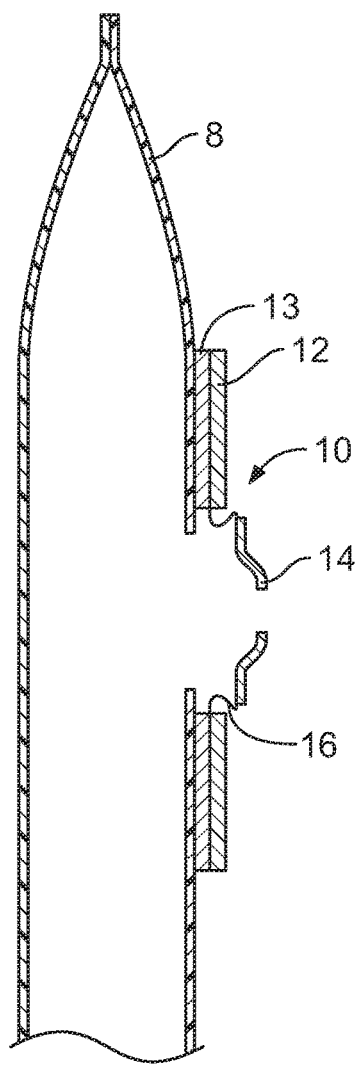
FIG. 5 is a cross-sectional view of the ostomy barrier of FIGS. 1-2 attached to a one-piece pouch system according to an embodiment.

Referring to FIGS. 1-2, an ostomy barrier according to an embodiment is shown. The ostomy barrier 10 may generally include an adhesive layer 12, a backing layer 13, a seal 14, and a flexible connector 16 between the adhesive layer 12 and the seal 14. The ostomy barrier 10 may have a body-facing side 18 for adhering to a user's skin (i.e., the skin of a wearer of the ostomy barrier) and a distal side 20 opposite to the body-facing side 18. In an embodiment, the ostomy barrier 10 may be configured as a faceplate assembly for a two-piece ostomy pouch system including a body-side coupling ring 30 arranged on the distal side 20 for engaging with a pouch-side coupling ring (not shown) as shown in FIG. 4. In another embodiment, the ostomy barrier 10 may be attached to a pouch 8 as shown in FIG. 5.

The adhesive layer 12 may include an adhesive or adhesives suitable for adhering to the user's skin for supporting an ostomy pouch as understood and known to those skilled in the art. The adhesive layer 12 and the backing layer 13 may also include an opening 22. The opening 22 may be substantially centrally positioned on the adhesive layer 12 and the backing layer 13, but is not limited to such a position. The adhesive layer 12 may be configured to be adhered to the user's abdomen with the stoma disposed in, or generally aligned with, the opening 22. In some embodiments, the adhesive layer 12 and the backing layer 13 may be formed from an adhesive coated nonwoven material, such as a nonwoven tape used in ostomy barriers as understood and known to those skilled in the art.

In one embodiment, the flexible connector 16 may be formed from an elastic material, such as an elastomer, and configured to connect the adhesive layer 12 and the seal 14. The flexible connector 16 may extend completely around a perimeter 24 of the opening 22 and extend inwardly therefrom. In one embodiment, the opening 22 may be substantially circular in shape and the flexible connector 16 extends radially inward from a perimeter 24 of the opening 22. It is understood, however, that the flexible connector 16 is not limited to the examples above. For example, the flexible connector 16 may be formed as a corrugated material or a material that is sized to loosely support the seal 14 in the opening 22 to allow movement of the seal 14 within the opening 22 and/or relative to the adhesive layer 12. In some embodiments, the flexible connector 16 may be made of a material suitable for sealing against leakage of effluent from the stoma, such as a suitable fabric material.

Figure 3:
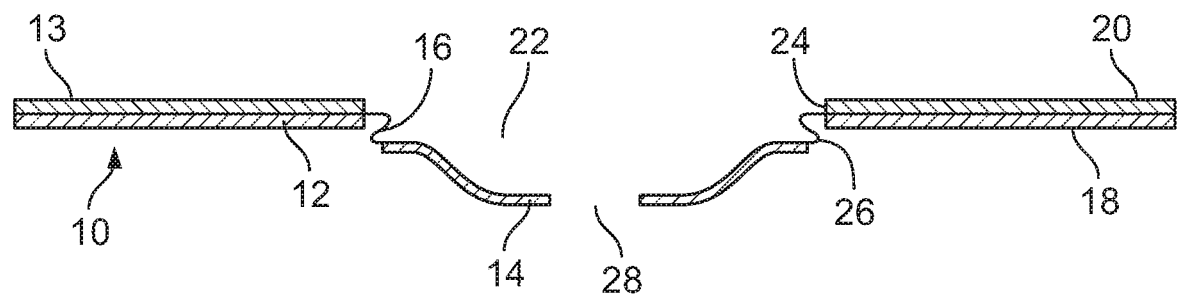
FIG. 3 is a perspective view showing an ostomy barrier according to another embodiment described herein.

The seal 14 may be connected to the flexible connector 16 and may be disposed within the opening 22 in a plan view of the ostomy barrier 10. The flexible connector 16 may extend about an outer periphery 24 of the seal 14 and may be connected to the seal 14 along the outer periphery 26 of the seal. In one embodiment, the seal 14 may be substantially circular in plan view, and extend radially within the flexible connector 16 and the opening 22 in the plan view. The seal includes an aperture 28 configured to receive the stoma (not shown). In one embodiment, the aperture 28 is substantially centered on the seal 14. The seal 14 is preferably formed of a soft, flexible material configured to engage and seal against the stoma, while providing adequate comfort to the user (i.e., the wearer). Suitable materials for the seal 14 may include hydrocolloid adhesives and other soft skin friendly adhesives. The seal 14 may also be formed from a moldable material. The seal 14 may have a generally convex shape or profile as shown in FIGS. 1-2. Alternatively, the seal 114 may have a generally flat profile as shown in FIG. 3.

The flexible connector 16 may be continuously and sealingly connected to the adhesive layer 12 and to the seal 14 to prevent or limit leakage of effluent from the stoma through the barrier 10. The flexible connector 16 may also overlap a portion of the adhesive layer 12 and/or the seal 14. For example, the flexible connector 16 may overlap the distal side 20. Alternatively, the flexible connector 16 may be connected to the perimeter 24 of the opening 22 and/or the outer periphery 26 of the seal 14 in a non-overlapping manner.

Referring to FIG. 2, the flexible connector 16 may be configured to allow the seal 14 to float relative to the adhesive layer 12 and the backing layer 13. In use, the body-facing side 18 of the adhesive layer 12 is adhered to the user's skin. The seal 14 is configured to engage the stoma around a perimeter of the seal aperture 28. Accordingly, the seal 14 may move with the stoma and the peristomal region while the adhesive layer 12 and the backing layer 13 remain adhered to the user's skin further out from the stoma. As shown in FIG. 2, for example, the seal 14 may move or float generally in an axial direction relative to the opening 22 in the adhesive layer 12. In one embodiment, the seal 14 may move through the opening 22 in the adhesive layer 12 and the backing layer 13 from the body-facing side 18 to the distal side 20.

Figure 6:
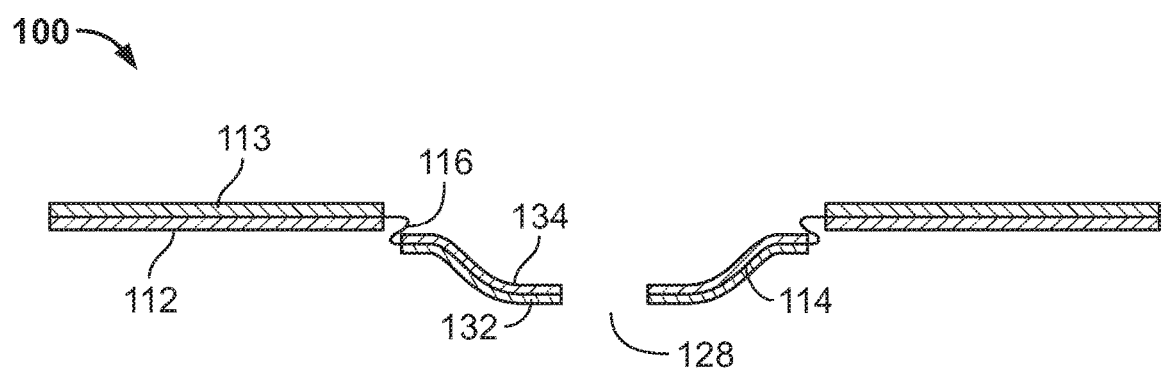
FIG. 6 is a cross-sectional view of an ostomy barrier according to yet another embodiment.

FIG. 6 is a cross-sectional view of an ostomy barrier according to an embodiment. The ostomy barrier 100 may be configured substantially the same as the ostomy barrier 10 described above, and generally include an adhesive layer 112, a backing layer 113, a seal 114, and a flexible connector 116. In this embodiment, the seal 114 may be a multilayer structure including an adhesive layer 132 and a reinforcement layer 134, and may have a generally convex profile. The adhesive layer 132 may be formed from a suitable skin friendly adhesive, such as a hydrocolloid adhesive. The reinforcement layer 134 may be formed from a suitable material, such as a thermoplastic polymer, and configured to maintain the convex profile of the seal 114. The reinforcement layer 134 may also be configured to have sufficient rigidity to provide a desired pressure against user's peristomal region. In use, the convexity of seal 114 may be directed toward the user, such that the seal 114 may apply pressure in the peristomal region on the user. This pressure may allow an otherwise retracted or flush stoma to protrude through the aperture 128 in the seal 114. Accordingly, effluent discharged from the stoma may be received in an attached ostomy pouch substantially without leakage between the user and the ostomy barrier 100. That is, the stoma may protrude through and sufficiently beyond the seal 114 to substantially prevent interaction or contact between the effluent from the stoma and the adhesive layer 112.

FIG. 3 is a perspective view showing an ostomy barrier 200 according to another embodiment described herein. The ostomy barrier 200 may be formed substantially the same as the ostomy barrier 10 described above, and generally include an adhesive layer 212, a seal 214, and a flexible connector 216. However, in this embodiment, a seal 214 may be formed having a generally flat profile. This configuration may be useful for a user having a protracted or extended stoma, for which pressure in the peristomal region may not be necessary. The seal 214 shown in FIG. 3 may float relative to the adhesive layer 212 similar to the seal 214 described in the embodiments above with respect to FIGS. 1 and 2.

Figure 7:
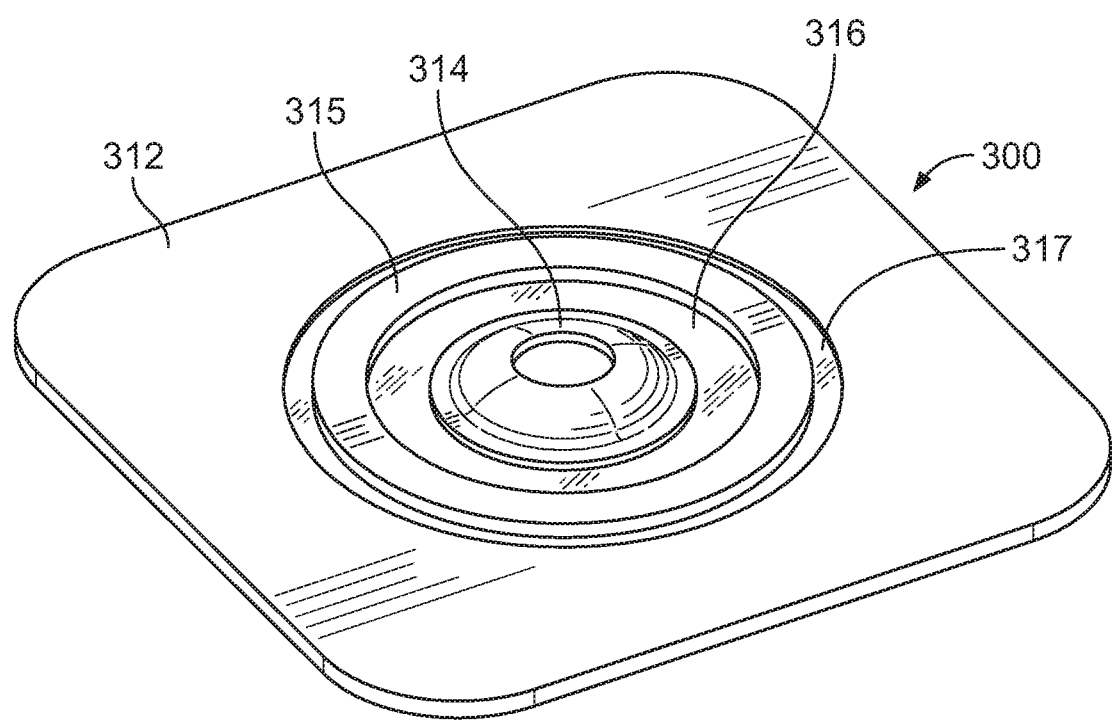
FIG. 7 is a perspective view of an ostomy barrier according an embodiment.

FIG. 7 is a perspective view of an ostomy barrier according to yet another embodiment. The ostomy barrier 300 may be formed similar to the ostomy barriers described in the embodiments above, but configured as a seal-in-seal ostomy barrier including an adhesive layer 312, first and second seals 314, 315 and first and second flexible connectors 316, 317. The first seal 314 may include a seal aperture 328 defined therein for receiving a stoma. The second seal 315 may be arranged between the first seal 314 and the adhesive layer 312. The first flexible connector 316 may be arranged and configured to connect the first and second seals 314, 315, while the second flexible connector 317 may be arranged and configured to connect the second seal 315 and the adhesive layer 312.

As it was with the ostomy barriers described in the foregoing embodiments, the first and second flexible connectors 316, 317 may be configured to allow the first and second seals 314, 315 to float. The first flexible connector 316 may be configured to allow the first seal 314 to float relative to the adhesive layer 312 and the second seal 315, and move with the stoma substantially independently from the adhesive layer 312 and the second seal 315. The second flexible connector 317 may be configured to allow the second seal 315 to float relative to the adhesive layer 312 and the first seal 314, and to allow the second seal 315 to move with the adjacent peristomal region substantially independently from the adhesive layer 312 and the first seal 314.

Each of the first and second seals 314, 315 may be configured to have a generally flat profile or a generally convex profile. In an embodiment, the first seal 314 may be configured to have a generally convex profile, while the second seal 315 may have a generally flat profile as shown in FIG. 7. In another embodiment, the first and the second seal 314, 315 may both be configured to have a generally flat profile, wherein the first seal 314 may have a greater thickness than the second seal 315, or the first and second seals 314, 315 may have a same thickness. In yet another embodiment, the second seal 315 may be provided on the adhesive layer 312 or fixedly attached to the adhesive layer 312 without the second flexible connector 317. In such an embodiment, only the first seal 314 may be configured to float relative to the rest of the ostomy barrier 300.

Accordingly, in the embodiments above, the function of sealing around the stoma and the function of supporting an ostomy pouch may be divided. For example, the adhesive layer 12, 112, 212, 312 may be adhered to the user's skin further out from the stoma to support an ostomy pouch, while the seal 14, 114, 214, 314, 315 may seal against the stoma and the peristomal region. The seal 14, 114, 214, 314, 315 is decoupled from the adhesive layer 12, 112, 212, 312 by way of the flexible connector 16, 116, 216, 316, 317 such that the seal 14, 114, 214, 314, 315 and the adhesive layer 12, 112, 212, 312 operate substantially independent of one another. Thus, the sealing function around the stoma and the support function of the adhesive may be optimized. As such, the barrier is more flexible than existing configurations and may move with the user's body. In addition, pressure to the skin surrounding the stoma may be reduced, and comfort of the user may be increased.

It is understood that the features described with respect to any of the embodiments above may be implemented, used together with, or replace features described in any of the other embodiments above.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. An ostomy barrier comprising:
an adhesive layer provided on a backing layer, the adhesive layer and the backing layer including an opening defined therein;
a seal substantially aligned with the opening, the seal having an aperture configured to receive a stoma therein; and
a flexible connector extending between the seal and the adhesive layer to connect the seal to the adhesive layer, wherein the seal and the flexible connector are separately formed members, wherein the flexible connector is connected to the adhesive layer at one end and extends radially inward from a perimeter of the opening and connected to the seal at an opposite end, the flexible connector formed from a flexible material to allow relative movement between the seal and the adhesive layer.

2. The ostomy barrier of claim 1, wherein the seal is convex in shape.

3. The ostomy barrier of claim 1, wherein the seal is generally flat.

4. The ostomy barrier of claim 1, wherein the flexible connector is formed from an elastic material.

5. The ostomy barrier of claim 1, wherein the seal is formed from a soft and flexible moldable material.

6. The ostomy barrier of claim 1, wherein the seal is formed from a hydrocolloid adhesive.

7. The ostomy barrier of claim 1, wherein the seal includes a seal adhesive layer and a reinforcement layer, wherein the reinforcement layer is formed to have a convex profile; and wherein the seal adhesive layer is arranged on a body-facing side of the reinforcement layer.

8. The ostomy barrier of claim 7, wherein the seal adhesive layer is formed from a hydrocolloid adhesive.

9. The ostomy barrier of claim 7, wherein the reinforcement layer is formed from a thermoplastic material.

10. The ostomy barrier of claim 1, wherein the ostomy barrier has a body-facing side and a distal side opposite the body-facing side, wherein the adhesive layer is arranged on the body-facing side and the backing layer is arrange on the distal side, wherein the seal is movable relative to the adhesive layer from the body-facing side to the distal side.

11. The ostomy barrier of claim 1, wherein the adhesive layer and the backing layer are formed from a nonwoven tape, wherein the adhesive layer is formed from a different material than a seal material.

12. An ostomy barrier comprising:
an adhesive layer provided on a backing layer, the adhesive layer and the backing layer including a first opening defined therein;
a first seal and a second seal, wherein the second seal is substantially aligned with the first opening and includes a second opening defined therein, wherein the first seal is substantially aligned with the second opening and includes an aperture configured to receive a stoma therein; and
a first flexible connector and a second flexible connector, wherein the first seal, the second seal, the first flexible connector, and the second flexible connector are four separate members, wherein the first flexible connector extends between the first seal and the second seal to connect the first seal to the second seal, and the second flexible connector extends between the second seal and the adhesive layer to connect the second seal to the adhesive layer, wherein each of the first and second flexible connectors is formed from a flexible material to allow relative movement between the first seal, the second seal, and the adhesive layer.

13. The ostomy barrier of claim 12, wherein each of the first and second seals is generally flat.

14. The ostomy barrier of claim 12, wherein the first seal has a convex shape and the second seal is generally flat.

15. The ostomy barrier of claim 12, wherein each of the first and second flexible connectors is formed from an elastic material.

16. The ostomy barrier of claim 12, wherein each of the first and second seals is formed from a soft and flexible moldable material.

17. The ostomy barrier of claim 12, wherein the ostomy barrier has a body-facing side and a distal side opposite the body-facing side, wherein the adhesive layer is arranged on the body-facing side and the backing layer is arrange on the distal side, wherein each of the first and second seal is movable relative to the adhesive layer from the body-facing side to the distal side.

18. An ostomy barrier comprising:
an adhesive layer provided on a backing layer, the adhesive layer and the backing layer including a first opening defined therein;
a first seal and a second seal, wherein the second seal is substantially aligned with the first opening and includes a second opening defined therein, wherein the first seal is substantially aligned with the second opening and includes an aperture configured to receive a stoma therein; and
a first flexible connector and a second flexible connector, wherein the first flexible connector extends between the first seal and the second seal to connect the first seal to the second seal, and the second flexible connector extends between the second seal and the adhesive layer to connect the second seal to the adhesive layer, wherein each of the first and second flexible connectors is formed from a flexible material to allow relative movement between the first seal, the second seal, and the adhesive layer, wherein each of the first and second seals is formed from a hydrocolloid adhesive.

19. An ostomy barrier comprising:
an adhesive layer provided on a backing layer, the adhesive layer and the backing layer including a first opening defined therein;
a first seal and a second seal, wherein the second seal is substantially aligned with the first opening and includes a second opening defined therein, wherein the first seal is substantially aligned with the second opening and includes an aperture configured to receive a stoma therein; and
a first flexible connector and a second flexible connector, wherein the first flexible connector extends between the first seal and the second seal to connect the first seal to the second seal, and the second flexible connector extends between the second seal and the adhesive layer to connect the second seal to the adhesive layer, wherein each of the first and second flexible connectors is formed from a flexible material to allow relative movement between the first seal, the second seal, and the adhesive layer, wherein the first seal includes a seal adhesive layer and a reinforcement layer, wherein the reinforcement layer is formed from a thermoplastic material having a convex profile, and the seal adhesive layer is arranged on a body-facing side of the reinforcement layer, wherein each of the seal adhesive layer and the second seal is formed from a hydrocolloid adhesive.

* * * * *